United States Patent [19]

Gehrig et al.

[11] Patent Number: 4,506,072

[45] Date of Patent: Mar. 19, 1985

[54] REGENERATION OF CAFFEINE-LOADED ACTIVATED CARBON WITH HOT WATER

[75] Inventors: Manfred Gehrig, Wolnzach; Manfred Barthels; Hans Wienges, both of Bremen, all of Fed. Rep. of Germany

[73] Assignee: Hag GF Aktiengesellschaft, German Democratic Rep.

[21] Appl. No.: 485,766

[22] Filed: Apr. 18, 1983

[51] Int. Cl.³ .......................................... C07D 473/12
[52] U.S. Cl. .................................... 544/274; 544/275
[58] Field of Search ................. 544/274, 275; 424/253

[56] References Cited

U.S. PATENT DOCUMENTS 4,298,736 11/1981 Katz et al. .......................... 544/275

*Primary Examiner*—Nicholas S. Rizzo
*Attorney, Agent, or Firm*—Linn I. Grim; Daniel J. Donovan

[57] ABSTRACT

The invention relates to a process for recovering caffeine adsorbed to activated carbon with simultaneous regeneration of the activated carbon in which the caffeine-loaded activated carbon is treated with water at a pressure of at least 86 bar and at a temperature of at least 300° C.

3 Claims, No Drawings

REGENERATION OF CAFFEINE-LOADED ACTIVATED CARBON WITH HOT WATER

TECHNICAL FIELD

The invention relates to a process for recovering caffeine adsorbed to activated carbon with simultaneous regeneration of the activated carbon in which the caffeine-loaded activated carbon is treated with water at a pressure of at least 86 bar and at a temperature of at least 300° C.

BACKGROUND ART

For health reasons the decaffeination of vegetable products has gained considerable significance. Moreover, the caffeine obtained as by-product can be profitably sold.

In several decaffeination processes the hydrolyzed coffee beans are decaffeinated by means of organic solvents. The recovery of the solvent is effected by distillation, for example, in the course of which the caffeine is obtained as by-product.

In order to avoid any contamination of the vegetable material by solvent residues, carbon dioxide has recently been used as extractant as it is unobjectionable under the health aspect (German Pat. Nos. 2,005,293 and 2,212,281). The carbon dioxide solvent in these processes is freed from dissolved caffeine by means of activated carbon.

Prior to re-use of spent activated carbon the adsorbed substances are normally pyrolyzed and thereafter the carbon is thermally reactivated. On account of the usefulness of caffeine such a method is uneconomical.

Therefore, efforts have been made to recover the adsorbed caffeine. In the selection of measures for desorption of caffeine it must be borne in mind that active carbon is a very good adsorbent, a circumstance which renders desorption difficult. Moreover, the use of any agent objectionable under the health aspect is to be avoided since the extraction was carried out with carbon dioxide for the very reason to exclude such agents. For efficient and economical regeneration of the activated carbon the solvent should have a high dissolving capacity for the adsorbed substance and good transporting properties for the substance; thereafter the mixture should be readily separable.

According to the teaching of German OS No. 2,544,116 the adsorbate is desorbed with supercritical gases, especially with carbon dioxide. Thereafter the dissolved adsorbate must be removed from the dissolving gas.

U.S. Pat. No. 4,298,736 describes a process in which caffeine adsorbed to activated carbon is desorbed with a food-grade liquid solvent which may be an organic acid or an alcohol. The process is preferably carried out above 100° C. with glacial acetic acid or with azeotropic mixtures of glacial acetic acid and second components.

After regeneration of the activated carbon with nonvolatile solvents the solvent must be separated from the activated carbon in any event with steam, for example. This necessarily calls for an additional step.

It is the problem underlying the invention to provide a simple and economical process for recovering caffeine adsorbed to activated carbon with simultaneous regeneration of the activated carbon; the desorption of caffeine from the activated carbon is to be effected with a food-grade agent.

DISCLOSURE OF THE INVENTION

This problem is solved by a process in which the desorption of the caffeine from the activated carbon is carried out with simultaneous regeneration of the activated carbon with water at a pressure of at least 86 bar, preferably at least 150 bar, and at a temperature of at least 300° C.

Caffeine has been known to be water-soluble up to a certain degree (the solubility is 1.3% at 15° C. and 4.6% at 40° C.); however, tests with hot water revealed that the desorption of caffeine from the activated carbon is virtually impossible under these conditions. With the present invention it has been surprisingly found that the activated carbon can be substantially completely freed from caffeine and the caffeine can be simultaneously recovered by means of water at a pressure of at least 86 bar, preferably at least 150 bar, and at a temperature of at least 300° C. A preferred temperature in carrying out the process is about 350° C., while a preferred pressure is about 200 bar. The period of treating the activated carbon ranges from about 1 to 3 hours; for desorption of caffeine with simultaneous regeneration of the activated carbon at least about 15 times, preferably about 20 times the amount of water, based on the weight of the caffeine-loaded activated carbon, should be used.

The individual measures such as pressure, temperature, amount of water and treating period can be easily selected by the expert from case to case in optimum correlation. It only need be considered that, although under more rigid conditions, i.e., excessively high pressure and temperature conditions and longer treating periods, the desorption of all the caffeine from the activated carbon is possible, this brings about the risk of excessive decomposition of the caffeine due to hydrolysis and/or thermal degradation.

The process of the invention can be carried out batchwise or continuously.

The activated carbon obtained with the process of the invention can be re-used immediately without requiring any additional treating step. The adsorption activity of the activated carbon diminishes only slightly from one recycle to the next. High temperature reactivation is required only after many times of recycling the activated carbon.

In the following example the below-described mode of operation was adopted:

Water heated to the desired temperature in an autoclave was forced by a pump through a bed of activated carbon to be subjected to extraction. The activated carbon was contained in a heatable steel tube. A regulating valve served as throttle and maintained a pressure which prevented vaporization of the water in the autoclave. Downstream of the throttle the solution was cooled and trapped in fractions.

EXAMPLE 50 grams of loaded activated carbon having a water content of 5.87% and caffeine proportion of 8.3% in dry condition were extracted at 345° C. and at 200 bar with 20 times the amount of water. The test lasted for 150 minutes. 75% of the adsorbed caffeine were found in the solution (0.29%); only 3.4% of the adsorbed caffeine remained on the activated carbon. After a period of 75 minutes and after a throughput of 10 times the amount of water 64% of the adsorbed caffeine had been extracted.

What is claimed:

1. A process for recovering caffeine adsorbed to activated carbon with simultaneous regeneration of the activated carbon, characterized in that the caffeine-loaded activated carbon is treated with water at a pressure of at least 86 bar and at a temperature of at least 300° C.

2. Process according to claim 1 in which, after sufficient desorption of caffeine, the temperature is raised to 350° C. to decompose the residual caffeine.

3. Process according to claim 1 in which the caffeine is recovered from the aqueous solution by evaporation, concentration by membranes, freezing, salting out, or by extraction with an organic solvent.

* * * * *

UNITED STATES PATENT AND TRADEMARK OFFICE
CERTIFICATE OF CORRECTION

PATENT NO. : 4,506,072

DATED : March 19, 1985

INVENTOR(S) : Manfred Gehrig et al.

It is certified that error appears in the above-identified patent and that said Letters Patent are hereby corrected as shown below:

On the title page

Assignee: Change "Hag GF Aktiengesellschaft, German Democratic Rep." to

--Hag GF Aktiengesellschaft, Federal Rep. of Germany--

Signed and Sealed this

Tenth Day of December 1985

[SEAL]

Attest:

Attesting Officer

DONALD J. QUIGG

Commissioner of Patents and Trademarks